United States Patent
Meyer

(10) Patent No.: US 7,476,229 B2
(45) Date of Patent: Jan. 13, 2009

(54) CARTRIDGE FOR AN INTRAOCULAR LENS

(75) Inventor: Rolf Meyer, Port (CH)

(73) Assignees: Anton Meyer & Co. AG (CH); Asico LLC., Westmont, IL (US)

( * ) Notice: Subject to any disclaimer, the term of this patent is extended or adjusted under 35 U.S.C. 154(b) by 49 days.

(21) Appl. No.: 10/816,948

(22) Filed: Apr. 5, 2004

(65) Prior Publication Data

US 2004/0199173 A1 Oct. 7, 2004

Related U.S. Application Data

(60) Provisional application No. 60/460,416, filed on Apr. 7, 2003.

(51) Int. Cl.
*A61F 9/00* (2006.01)
*A61F 2/16* (2006.01)

(52) U.S. Cl. .................................................. 606/107

(58) Field of Classification Search ............... 606/107; 623/6.12

See application file for complete search history.

(56) References Cited

U.S. PATENT DOCUMENTS

| | | | |
|---|---|---|---|
| 4,906,247 A | 3/1990 | Fritch | |
| 5,123,905 A | 6/1992 | Kelman | |
| 5,304,182 A | 4/1994 | Rheinish et al. | |
| 5,425,734 A | 6/1995 | Blake | |
| 5,468,246 A * | 11/1995 | Blake | 606/107 |
| 5,499,987 A | 3/1996 | Feingold | |
| 5,549,614 A | 8/1996 | Tunis | |
| 5,643,275 A | 7/1997 | Blake | |
| 5,643,276 A | 7/1997 | Zaleski | |
| 5,716,364 A * | 2/1998 | Makker et al. | 606/107 |
| 5,772,667 A * | 6/1998 | Blake | 606/107 |
| 5,944,725 A | 8/1999 | Cicenas et al. | |
| 6,143,001 A | 11/2000 | Brown et al. | |
| 6,336,932 B1 | 1/2002 | Figueroa et al. | |
| 6,371,960 B2 | 4/2002 | Heyman et al. | |
| 6,401,916 B2 | 6/2002 | Sakanishi | |
| 6,468,282 B2 | 10/2002 | Kikuchi et al. | |
| 6,471,708 B2 | 10/2002 | Green | |
| 6,491,697 B1 | 12/2002 | Clark et al. | |
| 6,497,708 B1 * | 12/2002 | Cumming | 606/107 |
| 6,500,181 B1 | 12/2002 | Portney | |
| 6,503,275 B1 * | 1/2003 | Cumming | 623/6.12 |

(Continued)

FOREIGN PATENT DOCUMENTS

EP 1 287 791 A1 3/2003

(Continued)

*Primary Examiner*—Todd E Manahan
*Assistant Examiner*—Amy T Lang
(74) *Attorney, Agent, or Firm*—Rothwell, Figg, Ernst & Manbeck, P.C.

(57) ABSTRACT

A cartridge for an intraocular lens (L) for use in an injector (I) has an at least approximately plane resting surface (4) for supporting the lens (L) in a partially folded or non-folded state, an arched surface (11) which adjoins the resting surface (4), and a sliding element (3) with which the partially folded or non-folded lens (L) supported on the resting surface (4) can be slid along the arched surface (11) and folded, in particular rolled. By means of this cartridge, an intraocular artificial lens can be brought to the smallest possible format in a simple manner and without damage to the lens.

16 Claims, 3 Drawing Sheets

U.S. PATENT DOCUMENTS

| | | |
|---|---|---|
| 6,540,754 B2 * | 4/2003 | Brady .................. 606/107 |
| 6,685,740 B2 | 2/2004 | Figueroa et al. |
| 6,712,848 B1 | 3/2004 | Wolf et al. |
| 6,786,911 B2 | 9/2004 | Mitomo et al. |
| 2002/0022881 A1 | 2/2002 | Figueroa et al. |
| 2002/0082609 A1 | 6/2002 | Green |
| 2002/0193805 A1 | 12/2002 | Ott et al. |
| 2003/0187455 A1 | 10/2003 | Kobayashi et al. |
| 2003/0209452 A1 | 11/2003 | Mitomo et al. |
| 2004/0015235 A1 | 1/2004 | Worst et al. |
| 2004/0059343 A1 | 3/2004 | Shearer et al. |
| 2004/0087963 A1 | 5/2004 | Ossipov et al. |
| 2004/0097956 A1 | 5/2004 | Oda |
| 2004/0116936 A1 | 6/2004 | Seil |
| 2004/0127911 A1 | 7/2004 | Figueroa et al. |
| 2004/0133212 A1 | 7/2004 | Makker et al. |
| 2004/0147938 A1 | 7/2004 | Dusek et al. |
| 2004/0199174 A1 * | 10/2004 | Herberger et al. .......... 606/107 |

FOREIGN PATENT DOCUMENTS

| | | |
|---|---|---|
| WO | WO 95/13022 A1 | 5/1995 |
| WO | WO 96/03924 A1 | 2/1996 |
| WO | WO 01/87186 A1 | 11/2001 |
| WO | WO 02/058596 A2 | 8/2002 |
| WO | WO 2004/010903 A1 | 2/2004 |

* cited by examiner

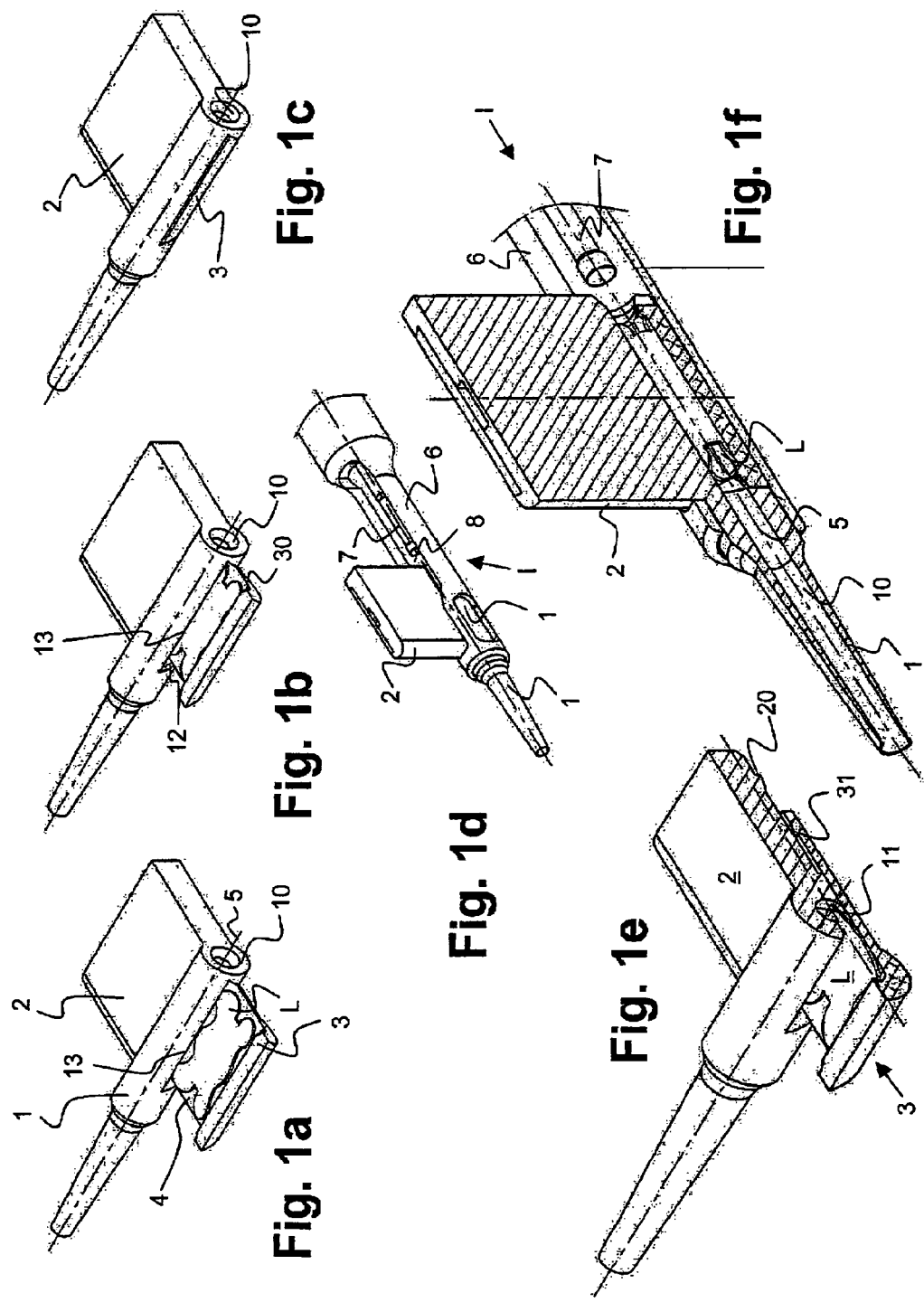

CARTRIDGE FOR AN INTRAOCULAR LENS

CROSS REFERENCE TO RELATED APPLICATIONS

This application claims priority from U.S. Provisional Application Ser. No. 60/460,416 filed on Apr. 7, 2003 the entire disclosure of which is incorporated herein by reference.

TECHNICAL FIELD

The invention relates to a cartridge for an intraocular lens for use in an injector.

STATE OF THE ART

In today's eye surgery field, the replacement of a blurred natural lens with an artificial lens is part of routine procedures. Implantation itself often takes place by means of an injector, such as is known for example from U.S. Pat. No. 5,643,276 and EP-A-1,287,791.

The injectors are in part equipped with devices for inserting the artificial lens more easily into the injector and folding it therein. Such devices are known for example from U.S. Pat. Nos. 6,143,001, 6,491,697, 5,944,725, 6,336,932, 6,371,960, WO 96/03924 and U.S. 2002/0022881.

Cartridges are also known in which the lens can be placed, folded and inserted into the injector along with the cartridge. Such cartridges are disclosed in WO 02/058596 and U.S. Pat. No. 5,499,987.

During eye surgery it is important that the patient's eye receives as small as possible an incision for introducing the lens. Therefore, it is advantageous if the tip of the injector that is inserted into the eye has as small a diameter as possible. The size of the diameter however is determined particularly by the size of the folded artificial lens which has to be pressed through this tip during injection into the eye.

DESCRIPTION OF THE INVENTION

It is an object of the invention to create a device with the aid of which an intraocular artificial lens can be brought to the smallest possible format in a simple manner and without damage to the lens.

This object is achieved with a cartridge comprising the features of patent claim 1.

The cartridge according to the invention enables a non-folded deformable lens to be placed onto a resting surface of the cartridge with a single pair of tweezers and the lens to be brought into a smaller format by means of a sliding element integrated into the cartridge. During the sliding process, the lens is preferably rolled. When the sliding element is completely inserted, the lens is preferably already located in the through-hole through which it is ejected during eye surgery by means of the injector. During rolling of the lens, the inner wall of the through-hole thus serves as a guide and determines the resulting diameter of the rolled lens.

Further advantageous embodiments are set out in the dependent patent claims.

BRIEF DESCRIPTION OF THE DRAWINGS

The following explains the subject of the invention based on preferred embodiments, which are depicted in the attached drawings. Equivalent parts have been marked with the same reference codes. In the drawing:

FIG. 1a shows a perspective view of a cartridge according to the invention in a first embodiment with inserted lens, but with the sliding element not inserted yet;

FIG. 1b shows the cartridge according to FIG. 1a with partially inserted sliding element;

FIG. 1c shows the cartridge according to FIG. 1a with completely inserted sliding element;

FIG. 1d shows the cartridge according to FIG. 1a during use in an injector;

FIG. 1e shows the cartridge according to FIG. 1a with partially inserted sliding element shown in a partial sectional view;

FIG. 1f shows a longitudinal section through FIG. 1d;

EMBODIMENTS OF THE INVENTION

Figure 2A:
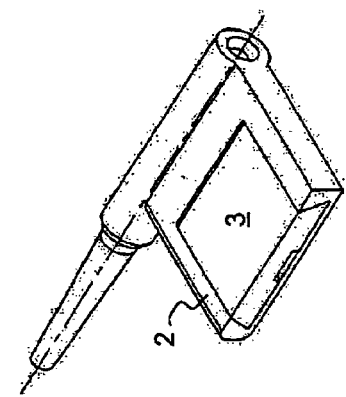
FIG. 2a shows a perspective view of a cartridge according to the invention in a second embodiment with inserted lens, but with the sliding element not inserted yet.

FIGS. 1a through 1e show a first embodiment of the cartridge according to the invention. A deformable lens L can be arranged in folded formation, preferably rolled up, in this cartridge. During use, the cartridge is inserted into an injector I, more specifically into an opening of the injector housing 6, and, by means of an injector piston 7, which is movable inside a through-hole 8 of the injector, the lens L is injected through the cartridge and into an eye of a patient. This can best be seen from FIG. 1f.

The cartridge has a hollow, regular cylindrical base body 1, a case 2 arranged thereon, a sliding element 3, a resting surface 4, and an arched surface 11 adjoining the resting surface.

The base body 1 defines a longitudinal axis 5 of the cartridge. A passage or through-hole 10 extends along this longitudinal axis 5. When the cartridge is fitted in the injector, this through-hole 10 is flush with a through-hole of the injector. In this example, the arched surface 11 is formed by an area of the through-hole 11 and is delimited thereby.

The case 2 is arranged on the base body, along a longitudinal side thereof. The sliding element 3 is arranged in a displaceably guided manner in the case 2, it being displaceable in a plane perpendicular to the longitudinal axis 5.

The sliding element 3 can preferably be removed in its entirety. However, embodiments are also possible in which it is held displaceably in the case 2 but cannot be removed from the latter without destroying it.

In the example shown here, the resting surface 4 is situated on the sliding element 3. The resting surface 4 is at least approximately plane and serves to support the lens L in the non-folded or only partially folded state. The resting surface 4 is made of a material with good sliding properties or is coated with a material having such properties.

The base body 1 comprises a groove 12 through which the sliding element 3 can be pushed in the direction of the case 2 and into the latter. A drawer is thus provided. The groove 12 is limited by an upper stop edge 13. When the sliding element 3 is pushed into the case 2, the lens L slides under this stop edge 13, guided on the sliding element. The resting surface 4 adjoins the arched surface 11, so that the lens L is folded or rolled in accordance with this arch when the sliding element 3 is pushed in.

The sliding element 3 preferably has an end surface or guiding surface 30 which is designed to ensure gentle sliding of the lens L. In particular, the end surface 30 can be curved. Additionally, or alternatively, it can be provided with a suitable coating and/or be made of a suitable material, in particular plastic. The rest of the cartridge is made at least in part, preferably entirely, of plastic.

In the folded or rolled state of the lens L, the sliding element 3 is preferably recessed into the case 2 such that it does not protrude on that side of the case 2 remote from the insertion area beyond the remaining wall of the cartridge.

The case 2 is designed as a holding element when inserting the cartridge in the injector, in order to facilitate insertion and removal of the cartridge. The cartridge can therefore be picked up, at the case, either by hand or with forceps and fitted into the injector and again removed from the latter.

In this example, the case 2 has an at least substantially closed design. In the examples described below, by contrast, the case 2 forms an at least approximately closed unit together with the inserted sliding element 3.

The sliding element 3 is preferably equipped with a snap-fit safety device which, when the sliding element 3 is in the inserted state, snaps into place and prevents the sliding element from shifting. In the example depicted here, this is a barb 31 which engages into a fastening nose 20 of the case 2.

Figure 2B:
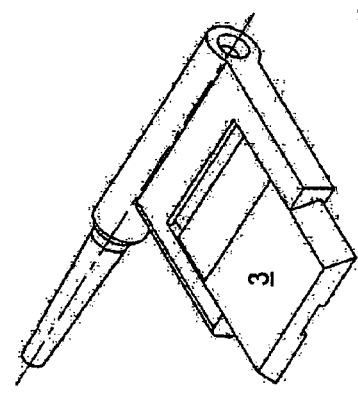
FIG. 2b shows the cartridge according to FIG. 2a with partially inserted sliding element.
Figure 2C:
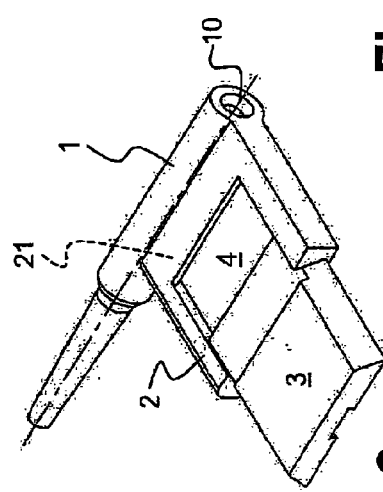
FIG. 2c shows the cartridge according to FIG. 2a with completely inserted sliding element.
Figure 2D:
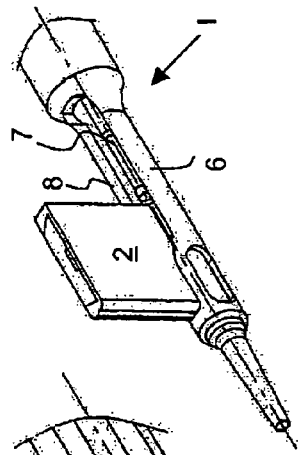
FIG. 2d shows the cartridge according to FIG. 2a during use in an injector.
Figure 2E:
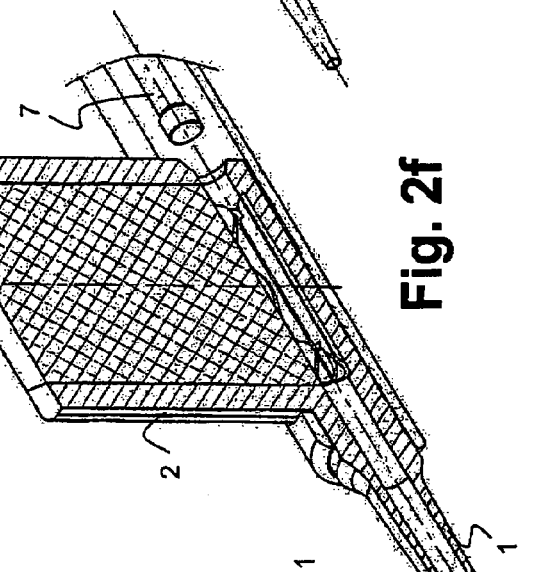
FIG. 2e shows the cartridge according to FIG. 2a with partially inserted sliding element shown in a partial sectional view.
Figure 2F:
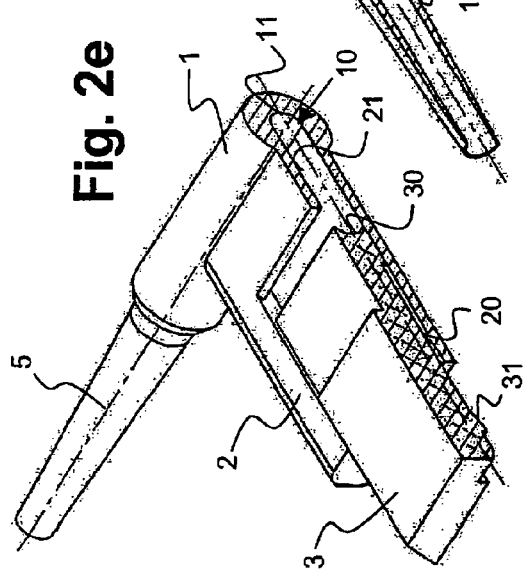
FIG. 2f shows a longitudinal section through FIG. 2d.

FIGS. 2a through 2e depict a second illustrative embodiment. Its function is essentially the same and will not be repeated here. In contrast to the previously described embodiment, however, the case 2 and the sliding element 3 are arranged on the same longitudinal side of the cartridge, and the resting surface 4 is formed by the case 2. In this second example, it is also possible to arrange the resting surface 4, as before, on the sliding element 3, so that it can be pushed together with the latter into the case 2.

The cartridge has a guiding surface 21 beneath which the lens L slides along in a guided manner for rolling or folding purposes. Said guiding surface 21 can be arranged on the base body 1 or, as is shown here, on the case 2. In the example described here, the guiding surface 21 is an inner, at least approximately plane surface of the case 2.

At least the base body 1 in the above-described first two illustrative embodiments has a single-piece design. In both examples, the case 2 is also preferably formed as a single piece on the base body 1 and thus represents an integral component part.

Figure 3C:
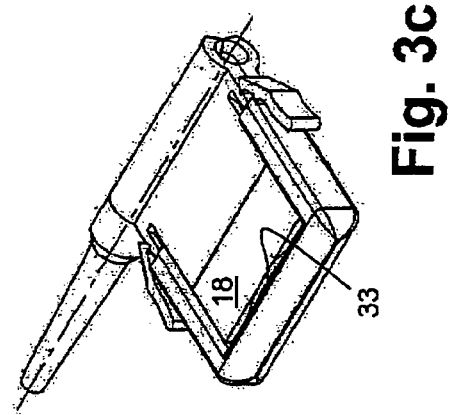
FIG. 3c shows the cartridge according to FIG. 3a with completely inserted sliding element.
Figure 3D:
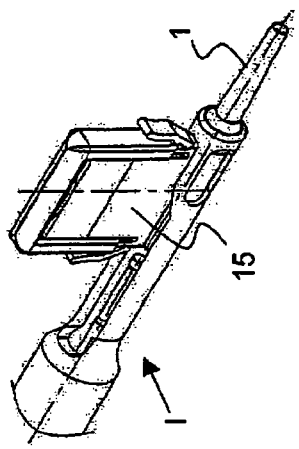
FIG. 3d shows the cartridge according to FIG. 3a during use in an injector.
Figure 3B:
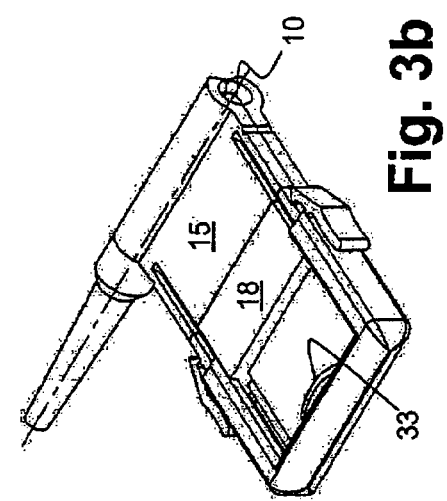
FIG. 3b shows the cartridge according to FIG. 3a with partially inserted sliding element.
Figure 3A:
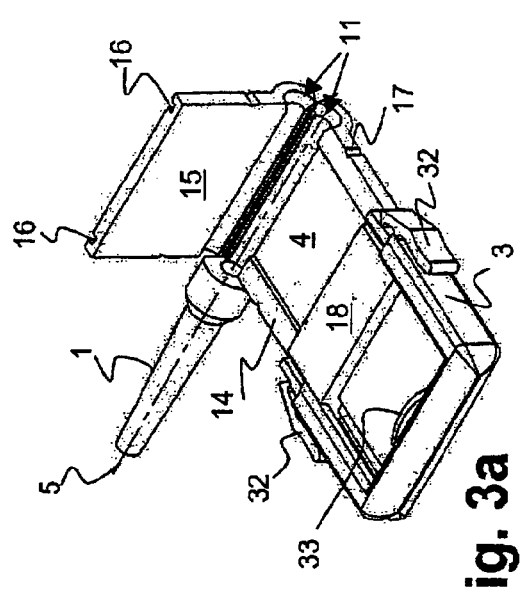
FIG. 3a shows a perspective view of a cartridge according to the invention in a third embodiment with inserted lens, but with the sliding element not inserted yet.
Figure 3E:
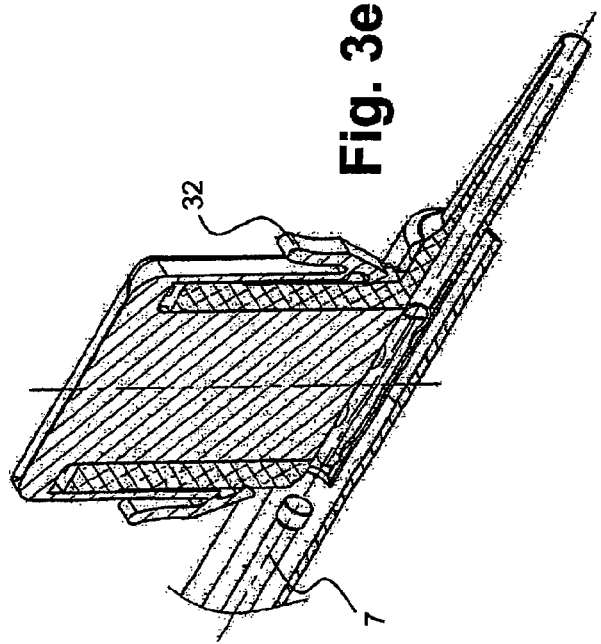
FIG. 3e shows a longitudinal section through FIG. 3d.

FIGS. 3a through 3d show a third illustrative embodiment. Here too, the function is once again the same. This embodiment, however, has the advantage that, when the sliding element 3 is pushed in, the cartridge can be opened once more and the position and integrity of the folded or rolled lens can be verified again.

Said cartridge comprises a base body 1 with two wings 14, 15 that can swivel parallel to the longitudinal axis 5. Said wings 14, 15 protrude like plates on a longitudinal side of the base body 1. The sliding element 3 is arranged on a first one of these two wings. The first wing 14 forms the resting surface 4. The second wing 15 can be folded onto the first wing 14, so that an inserted, non-folded lens L is arranged between the two wings 14, 15. The sliding element 3 can be pushed in between the two folded-together wings 14, 15 for the purpose of rolling or folding the lens L.

At least one of the wings 14, 15, preferably both, comprise outer guiding grooves 16, along which the sliding element 3 can be displaced in a guided manner.

The sliding element 3 is provided on at least one side, preferably on two opposite sides, with snap-fit catches 32 which, in the inserted state, engage in snap-fit grooves 17 arranged laterally on the wings 14, 15. Said snap-fit catches 32 are preferably detachable. One of the two wings, preferably the second wing 15, can be folded up again in the inserted state of the sliding element 3 in order to give an at least partial view of the rolled or folded lens L.

The first wing 14 furthermore has a stop element 18, in this case a raised end area, against which the sliding element 3 rests in the inserted state. In the sliding element 3 there is a spring element 33 which enables an elastic stop. In combination with the snap-fit catches 32 acting as snap-fit element, it is thus possible to ensure that the through-hole 10 of the cartridge is dimensionally flush with the through-hole 8 of the injector I.

By means of these cartridges, an intraocular artificial lens can be brought to the smallest possible format in a simple manner and without damage to the lens. Moreover, the folded lens in the cartridge can be optimally positioned in the injector.

REFERENCE LIST

1 Base Body
10 Through-Hole
11 Arched Surface
12 Groove
13 Upper Stop Edge
14 First Wing
15 Second Wing
16 Outer Guiding Groove
17 Snap-Fit Groove
18 Stop Element
2 Case
20 Fastening Nose
21 Guiding Surface
3 Sliding Element
30 End or Guiding Surface
31 Barb
32 Snap-Fit Catch
33 Spring Element
4 Resting Surface
5 Longitudinal Axis
6 Injector Housing
7 Injector Piston
8 Through-Hole of the Injector
I Injector
L Lens

The invention claimed is:

1. A cartridge for an intraocular lens for use in an injector, comprising:

a single-step or multiple-step hollow, regular cylindrical base body, and a case, for holding a sliding element, arranged on a first longitudinal side of the base body, wherein the sliding element is arranged on a second longitudinal side of the base body opposite the first longitudinal side, wherein an at least approximately plane resting surface for supporting the lens in a partially folded or non-folded state is arranged on the sliding element, wherein an arched surface adjoins the resting surface, and wherein the base body has a groove in which the sliding element can slide in the direction of the case so as to slide the partially folded or non-folded lens supported on the resting surface along the arched surface to fold or roll the lens.

2. The cartridge as claimed in claim 1, wherein the cartridge has a through-hole which, during use in the injector, is flush with a through-hole of the injector and through which the lens in its folded or rolled state can be injected into a patient's eye, and wherein the arched surface forms at least part of the through-hole of the cartridge.

3. The cartridge as claimed in claim 1, wherein the cartridge has a longitudinal axis along which the lens can be injected into a patient's eye, and wherein the sliding element can be displaced in a plane perpendicular to said longitudinal axis.

4. The cartridge as claimed in claim 3, wherein the case is designed as a holding element for holding the cartridge when inserting the latter into the injector.

5. The cartridge as claimed in claim 1, wherein the sliding element has a guiding surface for sliding the lens, wherein the guiding surface has at least one of the properties from the following group: it has a curved design, it is provided with a coating, it is made of plastic.

6. The cartridge as claimed in claim 1, wherein the sliding element is provided with a snap-fit safety device.

7. The cartridge as claimed in claim 1, wherein an upper stop edge is provided which limits a path of displacement of the sliding element into the case, wherein the lens, upon displacement of the sliding element, slides along in a guided manner under this stop edge for rolling or folding purposes.

8. The cartridge as claimed in claim 1, wherein the base body has a single-piece design.

9. A cartridge for an intraocular lens for use in an injector, comprising:
   a single-step or multiple-step hollow, regular cylindrical base body,
   an at least approximately plane resting surface for supporting the lens in a partially folded or non-folded state,
   an arched surface, located inside the body, adjoining the resting surface, and
   a sliding element to slide the partially folded or non-folded lens, supported on the resting surface, into the body and along the arched surface to fold or roll the lens,
   wherein a first and a second wing are arranged on the base body so as to swivel parallel to the longitudinal axis, said wings protruding like plates on a longitudinal side of the base body, and
   wherein the sliding element is slidably attached to said first wing.

10. The cartridge as claimed in claim 9, wherein the first wing forms the resting surface, and the second wing can be folded onto the first wing so that the lens supported on the resting surface is held between the two wings, and wherein the sliding element can be pushed in between the two folded-together wings for the purpose of rolling or folding the lens.

11. The cartridge as claimed in claim 10, wherein at least one of the wings has outer guiding grooves along which the sliding element can be displaced in a guided manner.

12. The cartridge as claimed in claim 9, wherein the sliding element is provided, on at least one side, with snap-fit catches which, in the inserted state, engage in snap-fit grooves arranged laterally on the wings.

13. The cartridge as claimed in claim 12, wherein the snap-fit catches are detachable.

14. A cartridge for an intraocular lens for use in an injector, comprising:
   a single-step or multiple-step hollow, regular cylindrical base body,
   an at least approximately plane resting surface for supporting the lens in a partially folded or non-folded state,
   an arched surface which adjoins the resting surface, and
   a sliding element to slide the partially folded or non-folded lens, supported on the resting surface, along the arched surface which folds the lens,
   wherein a first and a second wing are arranged on the base body so as to swivel parallel to the longitudinal axis, said wings protruding like plates on a longitudinal side of the base body, and
   wherein the sliding element is arranged on said first wing,
   wherein the first wing forms the resting surface,
   wherein the second wing can be folded onto the first wing so that the lens supported on the resting surface is held between the two wings,
   wherein the sliding element can be pushed in between the two folded-together wings for the purpose of rolling or folding the lens, and
   wherein the sliding element, in the inserted state, rests elastically against a stop element of the first wing.

15. A method for rolling or folding an intraocular lens, comprising:
   providing a cartridge comprising a single-step or multiple-step hollow, regular cylindrical base body, a first and a second wing arranged on the base body so as to swivel parallel to the longitudinal axis, said wings protruding like plates on a longitudinal side of the base body, said first wing having an at least approximately plane resting surface that supports the lens in a partially folded or non-folded state, said cartridge comprising an arched surface which adjoins the resting surface and a sliding element with which the partially folded or non-folded lens supported on the resting surface can be slid along the arched surface and folded or rolled;
   placing the intraocular lens in a partially folded or non-folded state on the resting surface;
   folding the second wing onto the first wing so that the lens supported on the resting surface is held between the two wings;
   pushing the sliding element in between the two folded-together wings so as to roll or fold the lens.

16. The cartridge as claimed in claim 9, wherein the sliding element remains attached to the first wing after the second wing swivels away from the first wing.

* * * * *